(12) United States Patent
Arendt

(10) Patent No.: US 8,727,774 B1
(45) Date of Patent: May 20, 2014

(54) DENTAL IMPLANT CARRIER DEVICE AND IMPLANT CARRIER DEVICE ASSEMBLY

(76) Inventor: Thomas Arendt, Norwalk, WI (US)

( * ) Notice: Subject to any disclaimer, the term of this patent is extended or adjusted under 35 U.S.C. 154(b) by 1 day.

(21) Appl. No.: 13/336,243

(22) Filed: Dec. 23, 2011

(51) Int. Cl.
*A61C 8/00* (2006.01)
(52) U.S. Cl.
USPC .................... 433/174; 433/173; 433/163
(58) Field of Classification Search
USPC ............. 433/172–176, 201.1, 163; 206/368
See application file for complete search history.

(56) References Cited

U.S. PATENT DOCUMENTS

| | | | |
|---|---|---|---|
| 5,049,073 A | 9/1991 | Lauks | |
| 5,312,254 A | 5/1994 | Rosenlicht | |
| 5,538,428 A | 7/1996 | Staubli | |
| 5,733,122 A * | 3/1998 | Gordon | 433/172 |
| 5,755,575 A | 5/1998 | Biggs | |
| 5,944,525 A | 8/1999 | Ura | |
| 5,964,591 A | 10/1999 | Beaty et al. | |
| 6,086,371 A | 7/2000 | Bassett et al. | |
| 6,159,008 A | 12/2000 | Kumar | |
| 6,203,323 B1 | 3/2001 | Beaty et al. | |
| 6,206,696 B1 | 3/2001 | Day | |
| 6,217,331 B1 | 4/2001 | Rogers et al. | |
| 6,217,332 B1 | 4/2001 | Kumar | |
| 6,315,562 B1 | 11/2001 | Kumar | |
| 6,394,809 B2 | 5/2002 | Rogers et al. | |
| 6,416,324 B1 | 7/2002 | Day | |
| 6,454,567 B1 | 9/2002 | Carchidi et al. | |
| 6,619,958 B2 | 9/2003 | Beaty et al. | |
| 6,951,462 B2 | 10/2005 | Kumar et al. | |
| 7,300,284 B2 | 11/2007 | Linder | |
| 7,344,376 B2 | 3/2008 | Beaty et al. | |
| 7,785,107 B2 * | 8/2010 | Niznick | 433/173 |
| 2003/0224327 A1 | 12/2003 | Constantino | |
| 2005/0191600 A1* | 9/2005 | Beaty et al. | 433/173 |
| 2007/0111163 A1 | 5/2007 | Powell et al. | |
| 2007/0281280 A1 | 12/2007 | Graham | |
| 2008/0153062 A1 | 6/2008 | Beaty et al. | |
| 2009/0253098 A1 | 10/2009 | Whipple | |
| 2010/0047741 A1 | 2/2010 | Blaim et al. | |
| 2010/0081112 A1* | 4/2010 | Better et al. | 433/174 |
| 2010/0167241 A1 | 7/2010 | Lombardi | |
| 2011/0306014 A1* | 12/2011 | Conte et al. | 433/173 |

* cited by examiner

*Primary Examiner* — Cris L Rodriguez
*Assistant Examiner* — Edward Moran
(74) *Attorney, Agent, or Firm* — Tipton L. Randall

(57) ABSTRACT

An implant carrier device for removable engagement with a dental implant includes a linear body member having first and second faceted exterior ends and an axial bore there through. A screw member having a head end and a threaded end is rotationally captured within the axial bore, with the threaded end extending exterior the second end of the carrier device. The threaded end of the screw member is adapted for rotational engagement of a threaded well within a dental implant. A dental implant engaged with both the faceted exterior second end of the linear body member and the threaded end of the captured screw member is partially driven into an osteotomy by way of the implant carrier device, followed by disengagement of the implant carrier device from the partially driven implant by rotation of the screw member captured within the axial bore of the implant carrier.

11 Claims, 10 Drawing Sheets

DENTAL IMPLANT CARRIER DEVICE AND IMPLANT CARRIER DEVICE ASSEMBLY

CROSS-REFERENCE TO RELATED APPLICATIONS, IF ANY

Not applicable.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates to dental implants and, more particularly, to an implant carrier device engagable with a dental implant and, most particularly, to a dental implant and implant carrier device assembly.

2. Background Information

The use of implants in dentistry has grown significantly over the past decades. The implant is generally a machined item that is secured within a drilled channel or osteotomy in the bone of a patient's mouth. The implant serves as a secure anchor upon which an abutment or artificial tooth is fastened. The implant includes a threaded exterior allowing the dentist to drive the implant into the osteotomy by rotating the implant. Care must be taken by the dentist to prevent contamination of the implant, thereby minimizing the occurrence of microbial infection in the osteotomy. The implant, abutment, and any tools or implements used in the process can be sterilized and kept sterile until use. However, handling of these items by the dentist during installation can result in contamination and the problems associated with it. Thus, it is highly desirable to minimize the direct handling of the implant and abutment during installation.

Applicant has devised an implant carrier device for attachment to an implant that minimizes the possibility of contamination and/or microbial infection that may occur during installation of a dental implant in the mouth of a patient.

SUMMARY OF THE INVENTION

The invention is directed to an implant carrier device adapted for removable engagement with a dental implant. The implant carrier device comprises a linear body member having first and second ends and an axial bore there through. The first end of the carrier device includes a faceted exterior surface, and the second end thereof includes a faceted exterior surface adapted for nonrotational engagement of a dental implant. A linear screw member having a head end and a threaded end is rotationally captured within the axial bore of the linear body member, with the threaded end thereof extending exterior the second end of the linear body member. The threaded end of the screw member is adapted for rotational engagement of a threaded well within a dental implant. A dental implant engaged with both the exterior second end of the linear body member and the threaded end of the captured screw member is partially driven into an osteotomy by means of the implant carrier device, followed by disengagement of the implant carrier device from the partially driven implant by rotation of the screw member captured within the axial bore of the implant carrier device.

A further embodiment of the invention is a dental implant and implant carrier device assembly. The assembly includes a cylindrical dental implant having first and second ends and a linear body member having a spiral thread on an exterior surface thereof. The second end of the dental implant has at least one bone chip cavity therein. The first end of the dental implant has an axial engagement well therein with two engagement features within the axial well. A cylindrical implant carrier device includes a linear body member having first and second ends and an axial bore there through. The first end thereof includes a faceted exterior surface, and the second end thereof including a faceted exterior surface for nonrotational engagement of the dental implant. A linear screw member has a head end and a threaded end. The screw member is rotationally captured within the axial bore of the linear body member, with the threaded end thereof extending exterior the second end of the linear body member. The threaded end of the screw member is rotationally engaged within the dental implant. A dental implant engaged with both the second end of the linear body member of the carrier device and the threaded end of the captured screw member is partially driven into an osteotomy by means of the implant carrier device, followed by disengagement of the implant carrier device from the dental implant by rotation of the screw member captured within the axial bore of the implant carrier device.

DESCRIPTION OF THE EMBODIMENTS

Nomenclature

Figure 1:
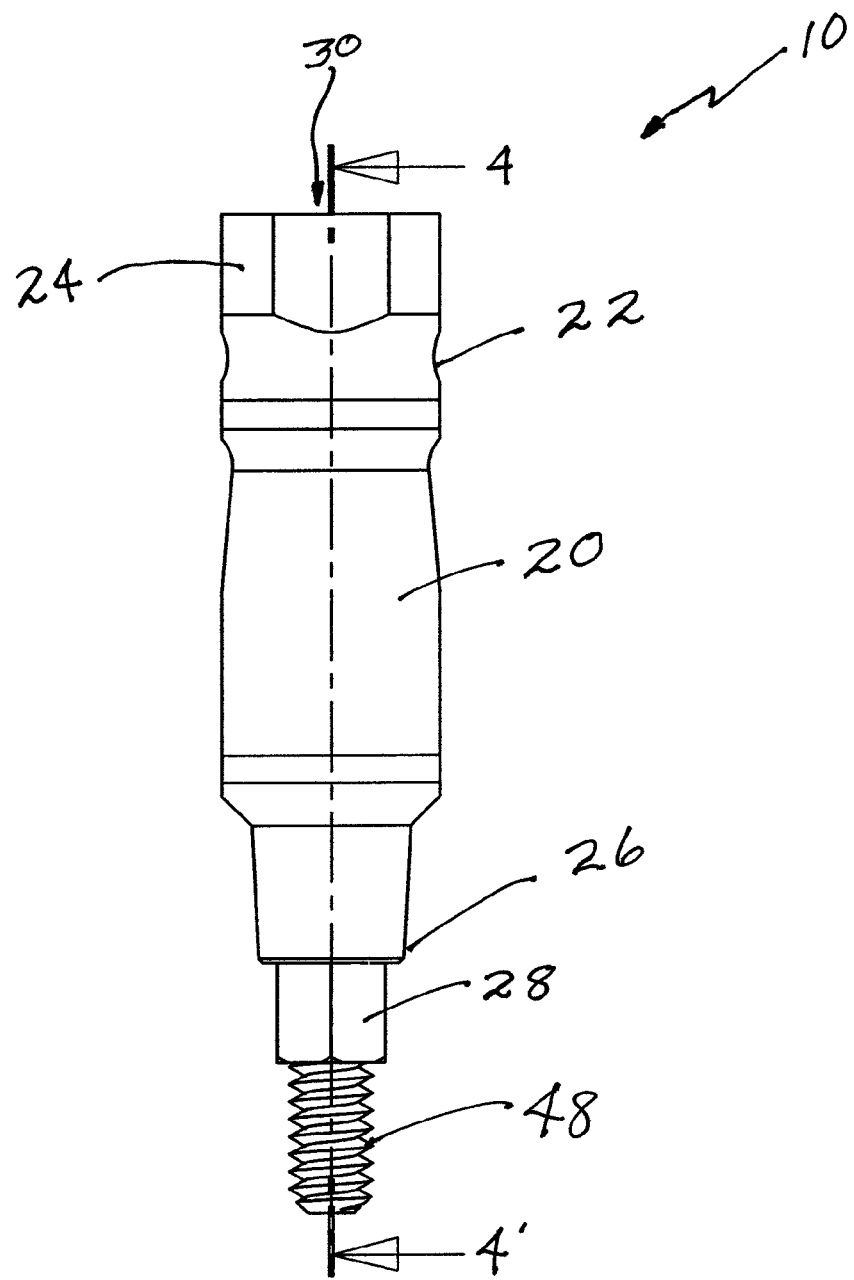
FIG. 1 is a perspective view of the dental implant carrier device of the present invention.

| | |
|---|---|
| 10 | Implant Carrier Device |
| 20 | Linear Body Member of Carrier |
| 22 | First End of Body Member |
| 24 | Faceted Exterior Surface of First End |
| 26 | Second End of Body Member |
| 28 | Faceted Exterior Surface of Second End |
| 30 | Axial Bore of Linear Body Member |
| 32 | Internal Shoulder of Axial Bore |
| 34 | Screw Capture Bushing |
| 36 | Axial Aperture of Capture Bushing |

DESCRIPTION OF THE EMBODIMENTS

| | |
|---|---|
| 40 | Linear Screw Member |
| 42 | Head End of Screw Member |
| 44 | Faceted Well of Head End |
| 46 | Shaft of Screw Member |
| 48 | Threaded End of Screw Member |
| 50 | Dental Implant |
| 60 | Linear Body Member |
| 62 | First End of Body Member |
| 64 | Second End of Body Member |
| 66 | Exterior Surface of Body Member |
| 68 | Spiral Thread on Exterior Surface |
| 70 | Bone Chip Cavity |
| 80 | Axial Engagement Well of Body Member |
| 85 | Threaded Engagement Feature of Axial Well |
| 90 | Faceted Surface Engagement Feature of Axial Well |
| 100 | Dental Implant and Implant Carrier Device Assembly |

CONSTRUCTION

The invention is an implant carrier device adapted for removable engagement with a dental implant. The implant carrier device comprises a linear body member having first and second ends and an axial bore there through. The first end of the carrier device includes a faceted exterior surface, and the second end thereof includes a faceted exterior surface adapted for nonrotational engagement of a dental implant. A linear screw member having a head end and a threaded end is rotationally captured within the axial bore of the linear body member, with the threaded end thereof extending exterior the second end of the linear body member. The threaded end of the screw member is adapted for rotational engagement of a threaded well within a dental implant. A dental implant engaged with both the exterior second end of the linear body member and the threaded end of the captured screw member is partially driven into an osteotomy by means of the implant carrier device, followed by disengagement of the implant carrier device from the partially driven implant by rotation of the screw member captured within the axial bore of the implant carrier device.

A further embodiment of the invention is a dental implant and implant carrier device assembly. The assembly includes a cylindrical dental implant having first and second ends and a linear body member having a spiral thread on an exterior surface thereof. The second end of the dental implant has at least one bone chip cavity therein. The first end of the dental implant has an axial engagement well therein with two engagement features within the axial well. A cylindrical implant carrier device includes a linear body member having first and second ends and an axial bore there through. The first end thereof includes a faceted exterior surface, and the second end thereof including a faceted exterior surface for nonrotational engagement of the dental implant. A linear screw member has a head end and a threaded end. The screw member is rotationally captured within the axial bore of the linear body member, with the threaded end thereof extending exterior the second end of the linear body member. The threaded end of the screw member is rotationally engaged within the dental implant. A dental implant engaged with both the second end of the linear body member of the carrier device and the threaded end of the captured screw member is partially driven into an osteotomy by means of the implant carrier device, followed by disengagement of the implant carrier device from the dental implant by rotation of the screw member captured within the axial bore of the implant carrier device.

Figure 2:
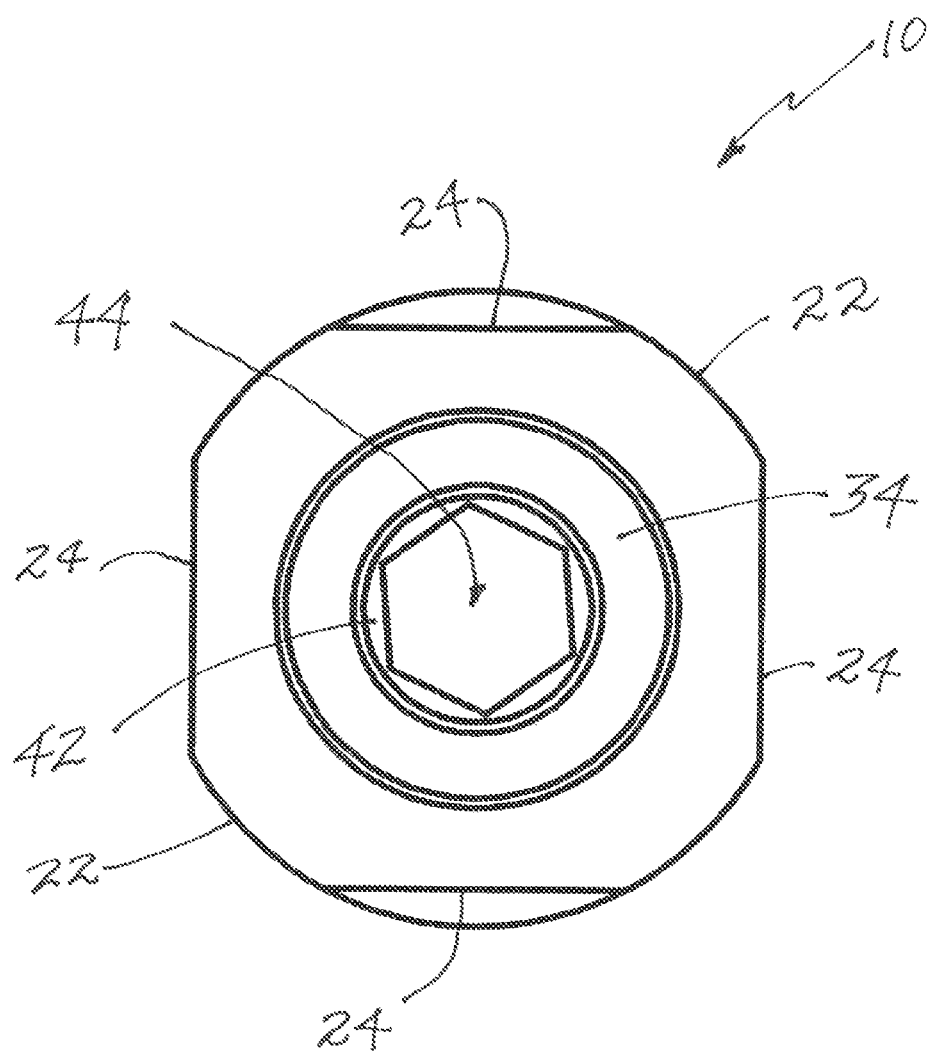
FIG. 2 is an enlarged top view of the dental implant carrier device of the present invention.
Figure 3:
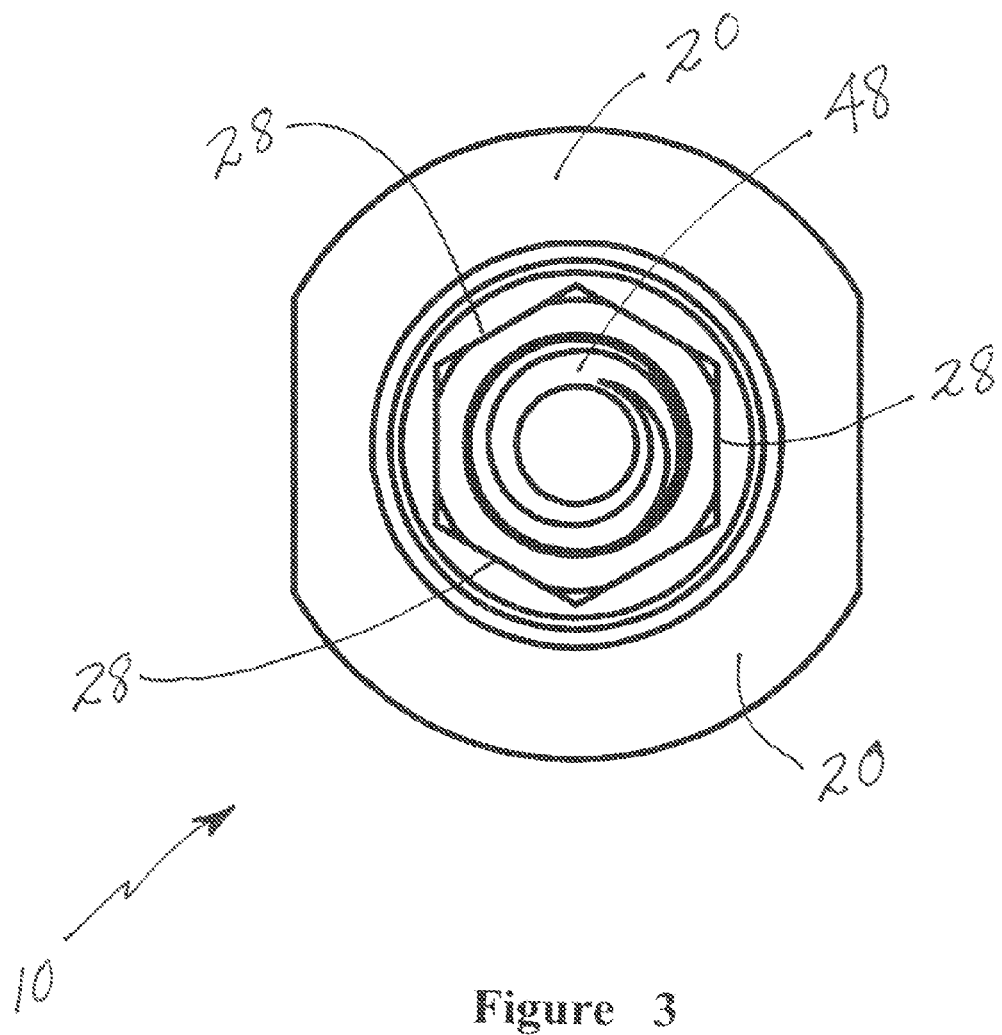
FIG. 3 is an enlarged bottom view of the dental implant carrier device of the present invention.
Figure 4:
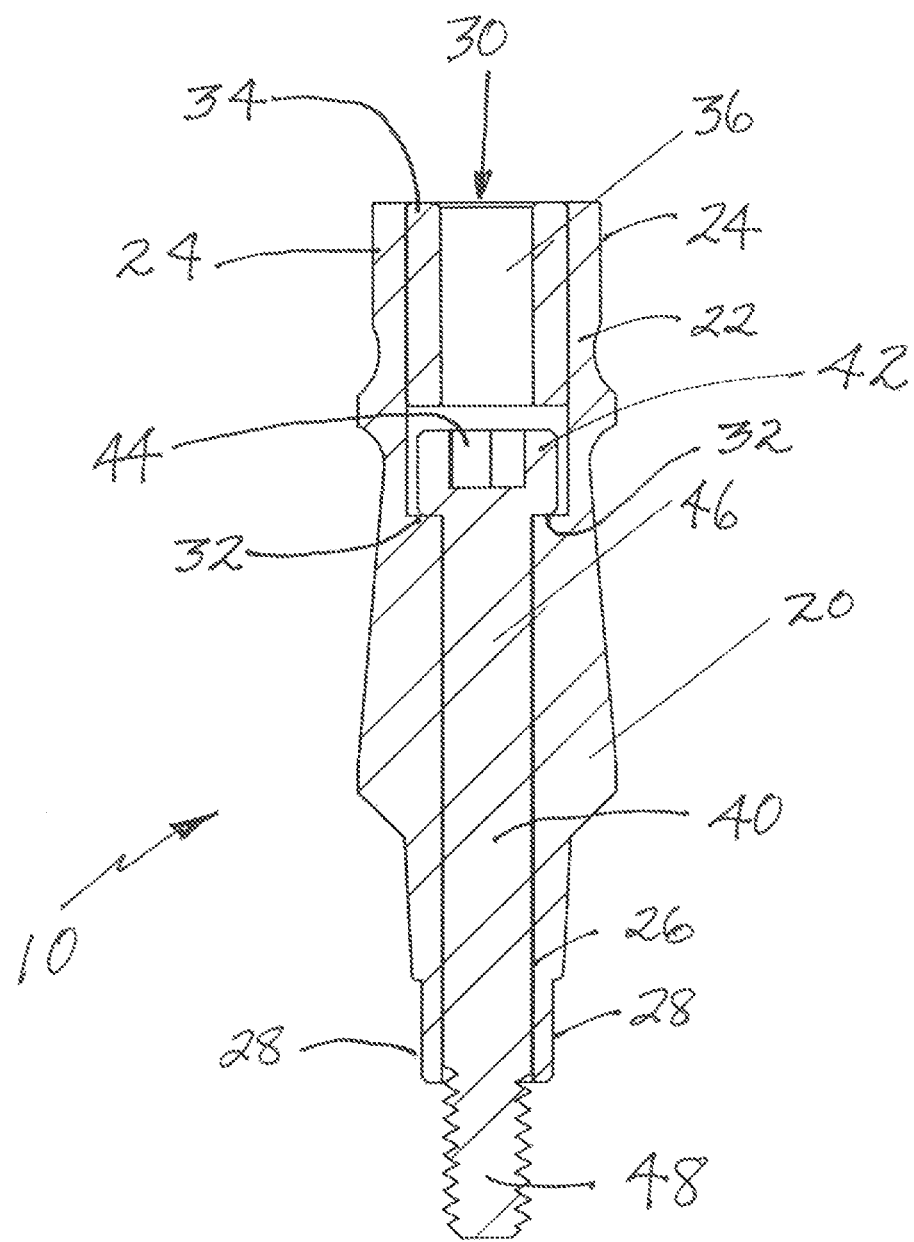
FIG. 4 is a sectional view along line 4-4' of FIG. 1 of the dental implant carrier device of the present invention.

Referring now to FIGS. 1-4, several views of the dental implant carrier device 10 are illustrated. The implant carrier device 10 comprises a linear body member 20 having a first end 22 and a second end 26 with an axial bore 30 from the first end 22 through the second end 26. The first end 22 of the implant carrier device 10 includes a faceted exterior surface 24 designed for mating with a tool that can rotate the device 10. The second end 26 thereof also includes a faceted exterior surface 28 adapted for nonrotational engagement of a dental implant 50, as described below. A linear screw member 40 having a head end 42 and a threaded end 48 is rotationally captured within the axial bore 30 of the linear body member, with the threaded end 48 thereof extending exterior the second end 26 of the linear body member 20. The axial bore 30 of the carrier device 10 includes an internal shoulder 32 upon which rests the head end 42 of the linear screw member 40, best seen in FIG. 4. The screw member 40 is retained within the axial bore 30 of the implant carrier device 10 by a screw capture bushing 34 that is press fitted into the axial bore 30 after insertion of the screw member 40 into the axial bore 30 of the carrier device 10, as shown in FIG. 4. The screw capture bushing 34 includes an axial aperture 36, providing access to the head end 42 of the screw member 40, which contains a faceted well 44 designed for mating with a tool that can rotate the captured screw member 40. Access to the faceted well 44 is best seen in FIG. 2, a top view of the carrier device 10. The threaded end 48 of the screw member 40 extending beyond the bottom end 26 of the implant carrier device 10 is adapted for rotational engagement of a threaded well 80 within a dental implant 50.

Figure 8:
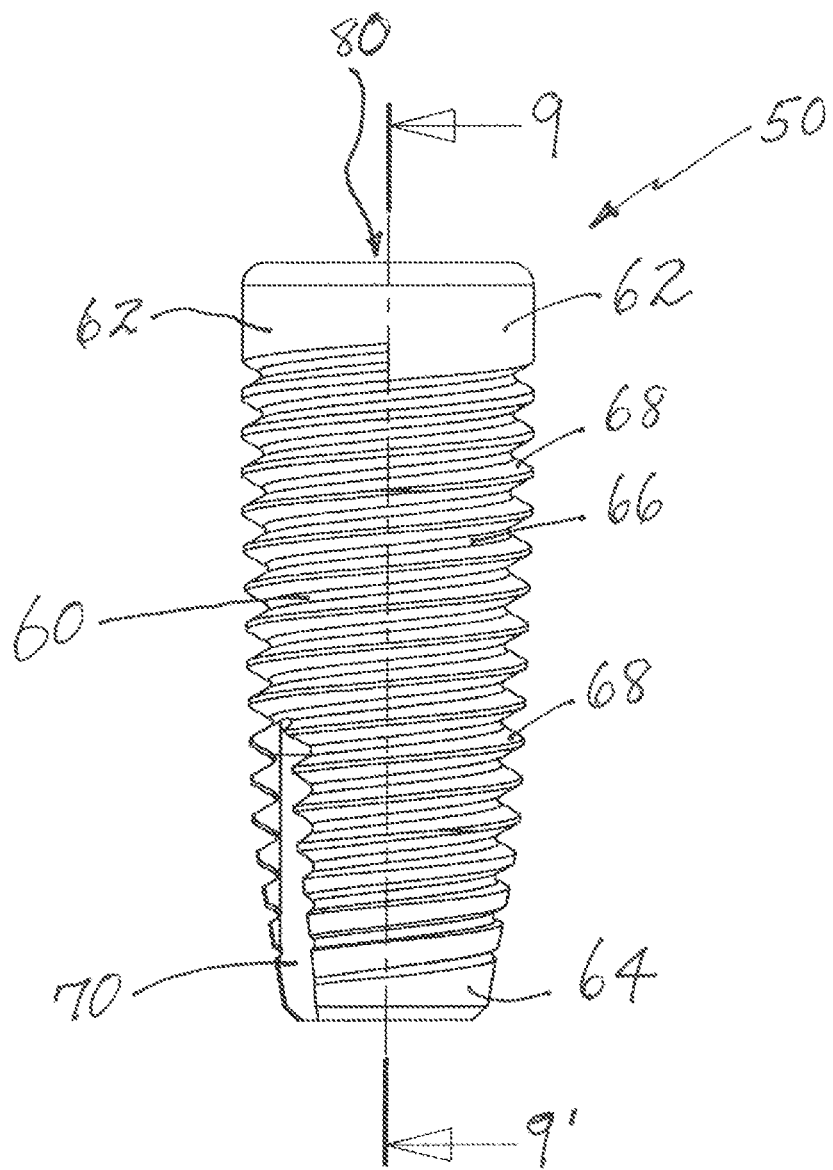
FIG. 8 is a perspective view of the dental implant of the present invention.
Figure 9:
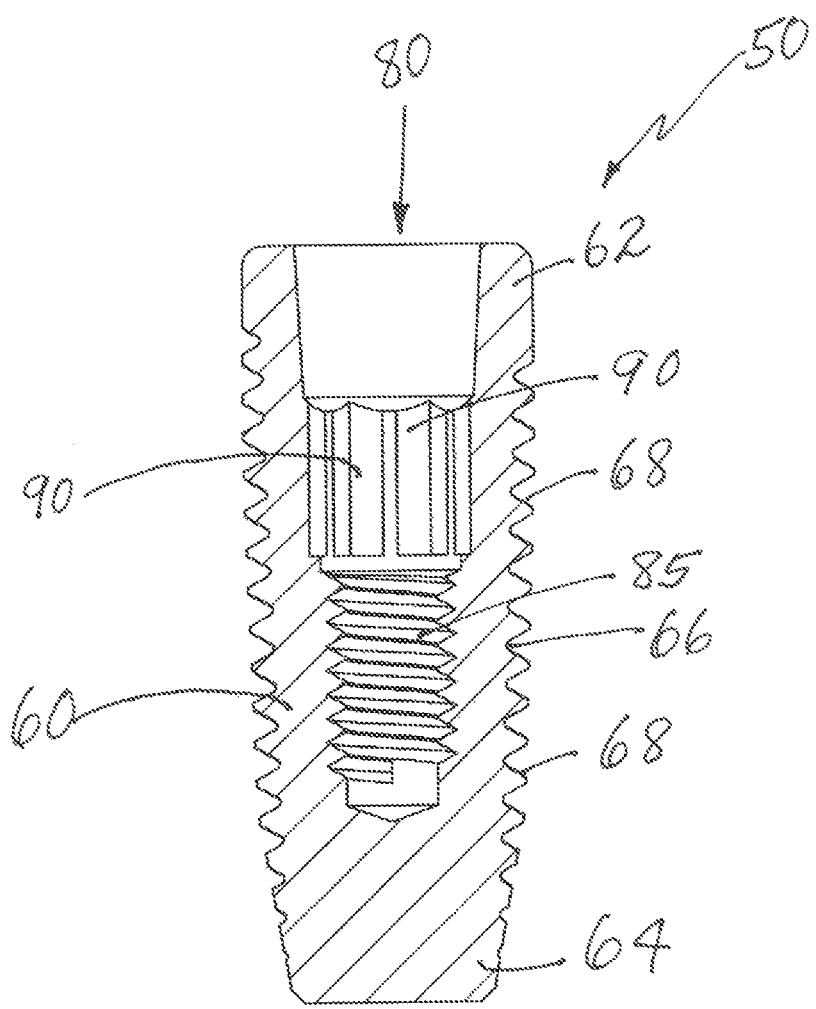
FIG. 9 is a sectional view along line 9-9' of FIG. 8 of the dental implant of the present invention.
Figure 10:
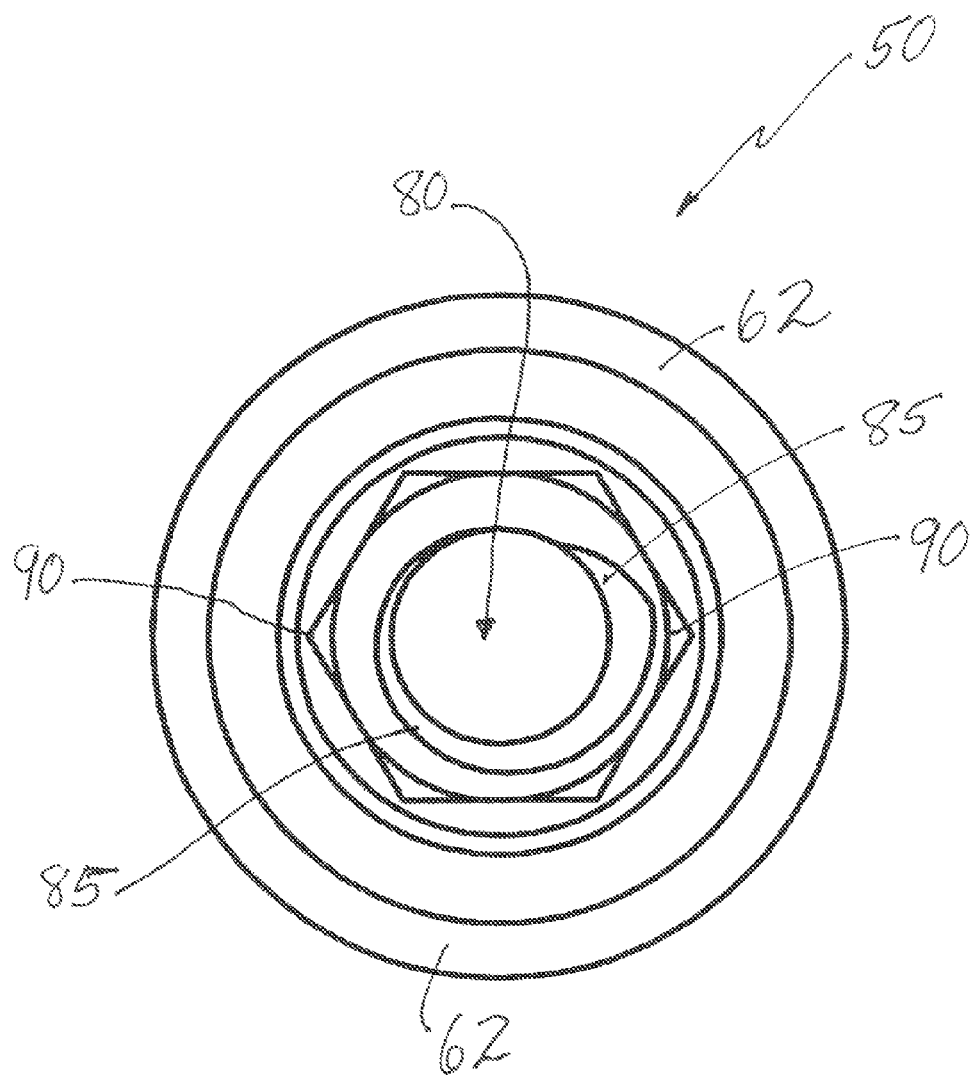
FIG. 10 is an enlarged top view of the dental implant of the present invention.

Referring now to FIGS. 8-10, a dental implant 50 designed for use with the implant carrier device 10 is illustrated. The dental implant 10 includes a cylindrical body member 60 having a first end 62 and a second end 64, the body member 60 including a spiral thread 68 on an exterior surface 66 thereof. An axial engagement well 80 extends from the first end 62 along the axis of cylindrical body member 60. The second end 64 of the body member 60 of the dental implant 50 has at least one bone chip cavity 70 therein. The axial engagement well 80 includes two interior engagement features there within. As shown in FIGS. 9 and 10, the engagement well 80 includes a threaded engagement feature 85 adjacent the closed end of the engagement well 80, and a faceted surface feature 90 adjacent the open top of the engagement well 80. The threaded engagement feature 85 is designed to engage the threaded end 48 of the screw member 40 extending beyond the second end 26 of the linear body member 20 of the implant carrier device 10. The faceted surface feature 90 is designed to engage the faceted exterior surface 28 of the second end 26 of the linear body member 20 of the implant carrier device 10.

Figure 5:
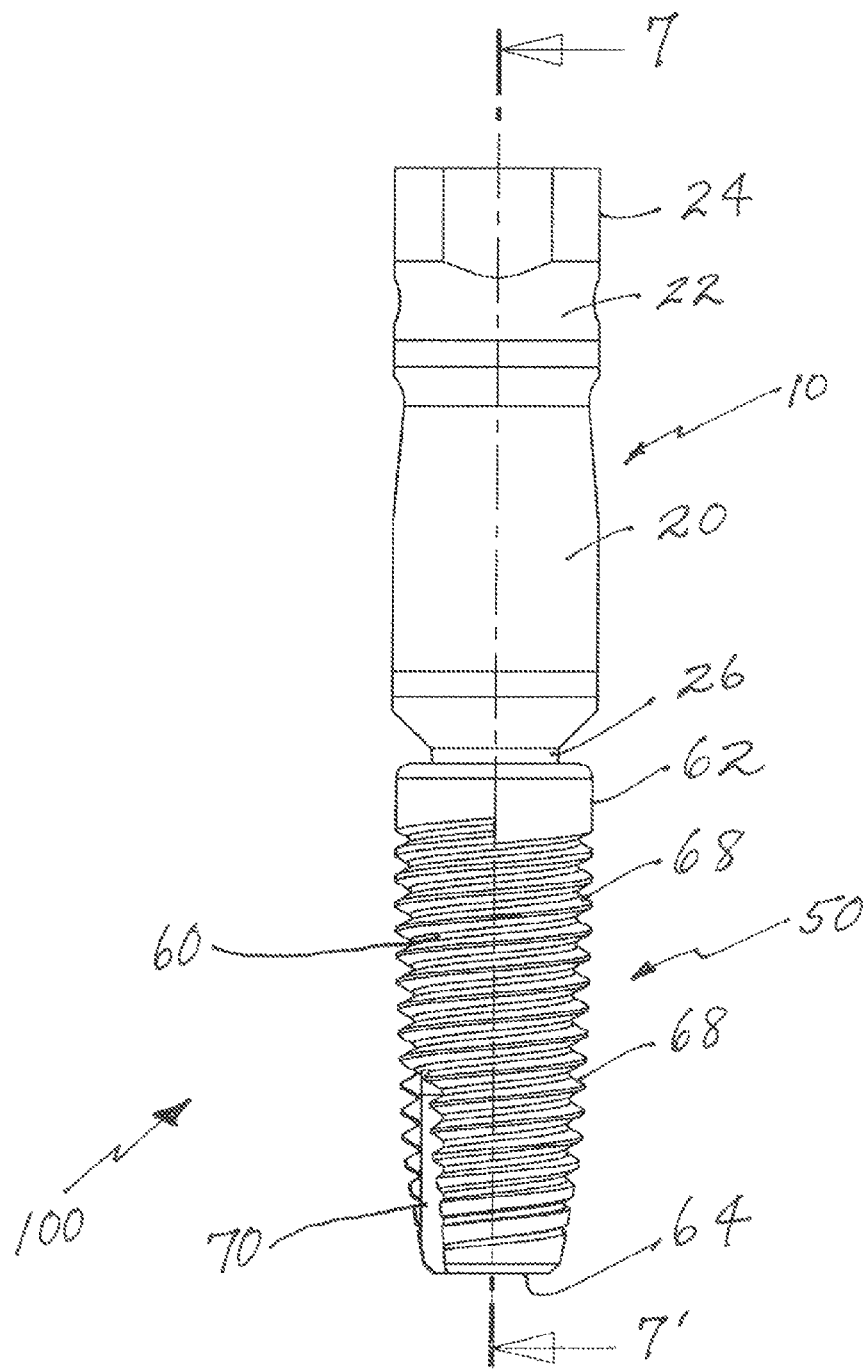
FIG. 5 is a perspective view of the dental implant and implant carrier device assembly of the present invention.
Figure 6:
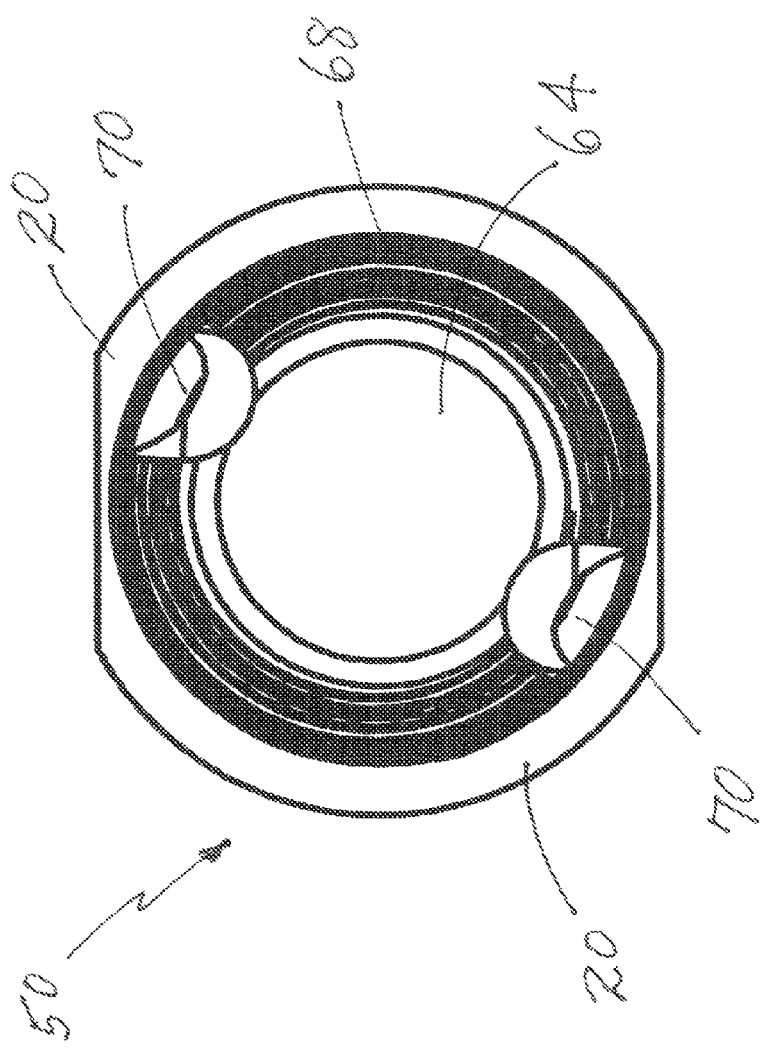
FIG. 6 is an enlarged bottom view of the dental implant and implant carrier device assembly of the present invention.
Figure 7:
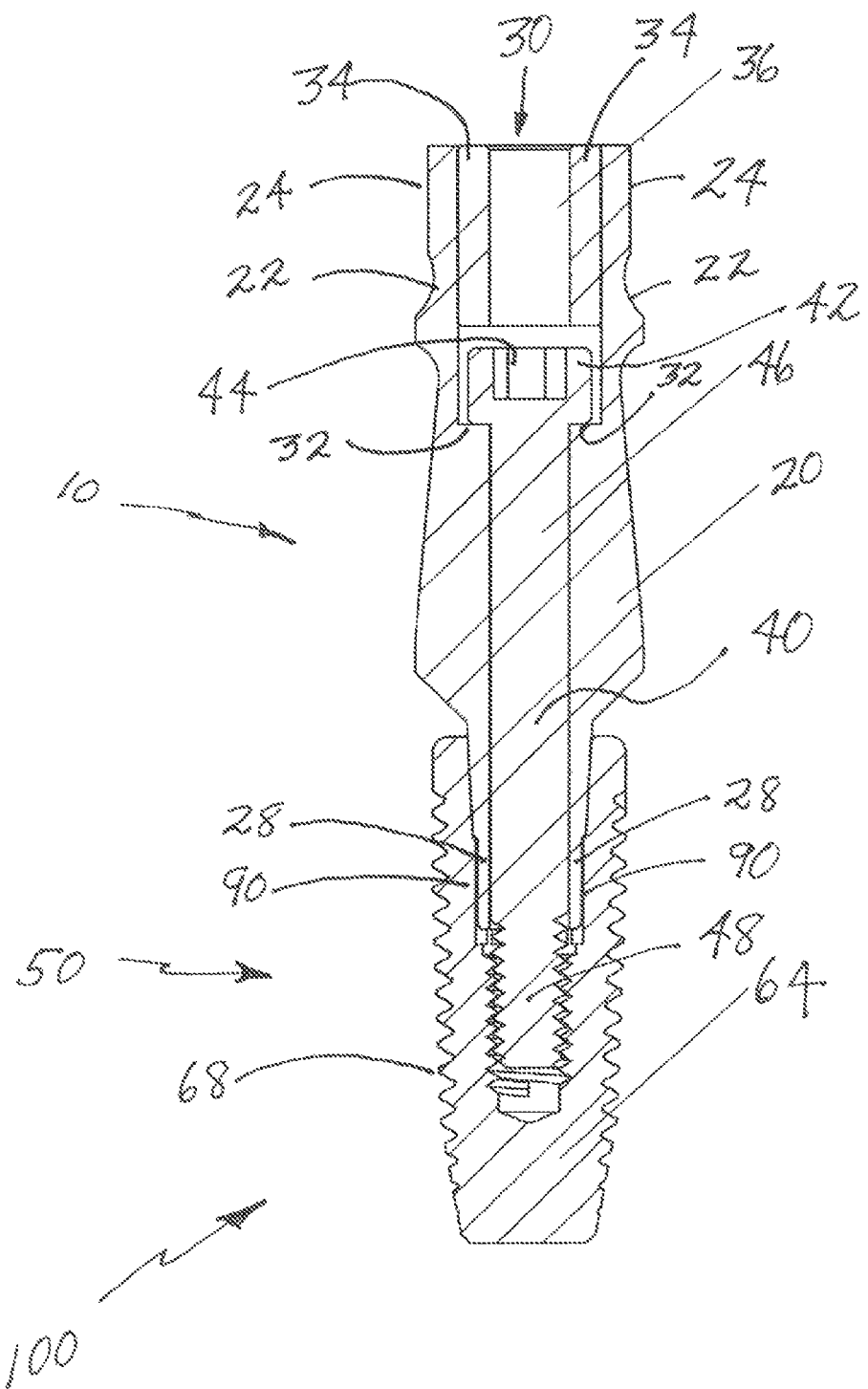
FIG. 7 is a sectional view along line 7-7' of FIG. 5 of the dental implant carrier device assembly of the present invention.

Referring now to FIGS. 5-7, the dental implant and implant carrier device assembly 100 of the present invention is illustrated. The assembly 100 is formed by inserting the second end 26 of the implant carrier device 10 into the axial engagement well 80 of the dental implant 50. The threaded end 48 of the screw member 40 extending exterior the second end 26 of the implant carrier device 10 engages the threaded engagement feature 85 adjacent the bottom end of the engagement well 80 of the dental implant 50. The second end 26 of the implant carrier device 10 is drawn into the engagement well 80 of the dental implant 50 by rotation of the screw member 40 with a tool inserted through the axial aperture 36 of the screw capture bushing 32. The faceted exterior surface 28 of the second end 26 of the body member 20 engages the faceted surface engagement feature 90 of the axial engagement well 80 of the implant body member 60 to provide non-rotatable coupling of the dental implant 50 and the implant carrier device 10.

In use, a dental implant 50, engaged with both the exterior second end 24 of the linear body member 20 and the threaded end 48 of the captured screw member 40, is partially driven into an osteotomy by means of a tool, such as a socket positioned over the first end 22 of the implant carrier device 10. Disengagement of the implant carrier device 10 from the partially driven dental implant 50 is achieved by rotation of the screw member 40 captured within the axial bore 30 of the implant carrier device 10. As the screw member 40 rotates to move upwardly and out of the threaded engagement feature 85 of the dental implant 50, the head end 42 of the screw member 40 contacts the capture bushing 34 and lifts the implant carrier device 10 out of the engagement well 80. When the screw member 40 disengages from the threaded engagement feature 85 of the dental implant 50, the carrier device 10 is free for removal from the partially driven implant 50 in the mouth of the patient. The partially driven dental implant 50 is then fully driven into the osteotomy with a sturdy tool that engages one or both of the engagement features 85, 90 within the axial engagement well 80 of the dental implant 50.

While the invention has been particularly shown and described with reference to preferred embodiments thereof, it will be understood by those skilled in the art that various changes in form and details may be made therein without departing from the spirit and scope of the invention.

I claim:

1. An implant carrier device adapted for removable engagement with a dental implant, the implant carrier device comprising:
    a linear body member having first and second ends and an axial bore there through, the first end thereof including a faceted exterior surface, the second end thereof including a faceted exterior surface adapted for nonrotational engagement of a dental implant;
    a linear screw member having a head end of selected diameter and a threaded end, the screw member rotationally captured within the axial bore of the linear body member by an internal shoulder supporting the head end of the linear screw member and by a capture bushing in the form of a cylinder press fitted within the axial bore, adjacent the first end of the linear body member, the capture bushing including an axial aperture of selected diameter less than the selected diameter of the head end of the screw member, the axial aperture accessing the head end of the screw member, with the threaded end of the screw member extending exterior the second end of the linear body member, the threaded end of the screw member adapted for rotational engagement of a threaded well of a dental implant;
    whereby a dental implant engaged with both the exterior second end of the linear body member and the threaded end of the captured screw member is partially driven into an osteotomy by means of the implant carrier device, followed by disengagement of the implant carrier device from the partially driven implant by rotation of the screw member captured within the axial bore of the implant carrier device by a tool engaging the head end thereof, the head end of the screw member contacting the capture bushing press fitted and fully inserted within the axial bore to forcibly lift the implant carrier out of the implant.

2. The implant carrier device adapted for removable engagement with a dental implant of claim 1, wherein the head end of the screw member includes a faceted well adapted for mating with a tool for rotation of the linear screw member.

3. The implant carrier device adapted for removable engagement with a dental implant of claim 1, wherein the second end of the linear body member includes a tapered section above the faceted exterior surface thereof.

4. The implant carrier device adapted for removable engagement with a dental implant of claim 3, wherein the tapered section of the second end of the linear body member includes a Morse taper.

5. A dental implant and implant carrier device assembly comprising;
    a cylindrical dental implant having first and second ends and a linear body member having a spiral thread on an exterior surface thereof, the second end of the dental implant having at least one bone chip cavity therein, the first end of the dental implant having an axial engagement well therein with two engagement features within the axial well;
    a cylindrical implant carrier device including a linear body member having first and second ends and an axial bore there through, the first end thereof including a faceted exterior surface, the second end thereof including a faceted exterior surface for nonrotational engagement of the dental implant;
    a linear screw member having a head end of selected diameter and a threaded end, the screw member rotationally captured within the axial bore of the linear body member by an internal shoulder supporting the bead end of the linear screw member and by a capture bushing in the form of a cylinder press fitted within the axial bore, adjacent the first end of the linear body member, the capture bushing including an axial aperture of selected diameter less than the selected diameter of the head end of the screw member, the axial aperture accessing the head end of the screw member, with the threaded end of the screw member extending exterior the second end of the linear body member, the threaded end of the screw member rotationally engaged within the dental implant;
    whereby a dental implant engaged with both the second end of the linear body member of the carrier device and the threaded end of the captured screw member is partially driven into an osteotomy by means of the implant carrier device, followed by disengagement of the implant carrier device from the dental implant by rotation of the screw member captured within the axial bore of the implant carrier device by a tool engaging the head end thereof, the head end of the screw member contacting the capture bushing press fitted and fully inserted within the axial bore to forcibly lift the implant carrier out of the engagement well.

6. The dental implant and implant carrier device assembly of claim 5, wherein the head end of the screw member includes a faceted well adapted for mating with a tool for rotation of the linear screw member.

7. The dental implant and implant carrier device assembly of claim 5, wherein the second end of the linear body member includes a tapered section above the faceted exterior surface thereof.

8. The dental implant and implant carrier device assembly of claim 7, wherein the tapered section of the second end of the linear body member includes a Morse taper.

9. An implant carrier device adapted for removable engagement with a dental implant, the implant carrier device comprising:
    a linear body member having first and second ends and an axial bore there through, the first end thereof including a:

faceted exterior surface, the second end thereof including a faceted exterior surface adapted for no/rotational engagement of a dental implant;

a linear screw member having a head end of selected diameter and a threaded end, the screw member rotationally captured within the axial bore of the linear body member by an internal shoulder supporting the head end of the linear screw member and a capture bushing in the form of a cylinder press fitted within the axial bore, adjacent the first end of the linear body member, the capture bushing including an axial aperture of selected diameter less than the selected diameter of the head end of the screw member, the axial aperture accessing a faceted well in the head end of the screw member, the threaded end of the screw member extending exterior the second end of the linear body member and adapted for rotational engagement of a threaded well of a dental implant;

whereby a dental implant engaged with both the exterior second end of the linear body member and the threaded end of the captured screw member is partially driven into an osteotomy by means of the implant carrier device, followed by disengagement of the implant carrier device from the partially driven implant by rotation of the screw member captured within the axial bore of the implant carrier device by a tool mating with the faceted well thereof, the head end of the screw member contacting the capture bushing press fitted and fully inserted within the axial bore to forcibly lift the implant carrier out of the implant.

10. The implant carrier device of claim 9, wherein the second end of the linear body member includes a tapered section above the faceted exterior surface thereof.

11. The implant carrier device of claim 10, wherein the tapered section of the second end of the linear body member includes a Morse taper.

* * * * *